United States Patent [19]
Theriault

[11] Patent Number: 5,607,973
[45] Date of Patent: Mar. 4, 1997

[54] METHOD OF TREATING TRAUMATIC CNS TISSUE INJURY WITH A METABOTROPIC GLUTAMATE RECEPTOR AGONIST

[76] Inventor: Elizabeth Theriault, Playfair Neuroscience Unit, The Toronto Western Hospital, 399 Bathurst Street, Toronto, Canada, M5T 2S8

[21] Appl. No.: 496,065

[22] Filed: Jun. 28, 1995

[51] Int. Cl.$^6$ .......................... A61K 31/195; A61K 31/19
[52] U.S. Cl. ............................................. 514/561; 514/567
[58] Field of Search ..................................... 514/561, 567

[56] References Cited

U.S. PATENT DOCUMENTS 5,500,420  3/1996  Maiese ..................................... 514/131

OTHER PUBLICATIONS

Birrell et al, *Chemical Abstracts*, vol. 120, No. 9, Abstract 95587e, 1994, p. 119.

*Primary Examiner*—Marianne M. Cintins
*Assistant Examiner*—William R. A. Jarvis
*Attorney, Agent, or Firm*—Cushman Darby & Cushman IP Group Pillsbury Madison & Sutro LLP

[57] ABSTRACT

A method for in vivo reducing the deleterious effect of traumatic CNS tissue injury by applying to said tissue a therapeutically effective amount of a metabotropic glutamate receptor agonist, preferably, trans-1-amino-1,3-cyclopentanedicarboxylic acid. The metabotropic glutamate receptor agonist activates a mGluR subtype, for example the mGluR-1α subtype.

6 Claims, 4 Drawing Sheets

Dorsal Column Segment (including adjacent dorsal horn gray matter)

Pre-injury

Control

Post-injury amplitude

Control latency 2 mV

1 μs    100 nM Trans-ACPD 100 nM Trans-ACPD

METHOD OF TREATING TRAUMATIC CNS TISSUE INJURY WITH A METABOTROPIC GLUTAMATE RECEPTOR AGONIST

FIELD OF THE INVENTION

This invention relates to a method of reducing the damaging effect of a traumatic injury to mammalian CNS tissue, particularly spinal cord tissue, by in vivo treatment thereof with a metabotropic glutamate receptor agonist; and pharmaceutical compositions comprising said agonists.

BACKGROUND TO THE INVENTION

Acute, traumatic spinal cord injury (SCI) is a devastating clinical condition for which there is currently no effective treatment. It usually results in lifelong disability for the patient and its effect is enormous in terms of the psychological, social, and financial costs to the patient, the family and society. The neurological deficits resulting from SCI are often progressive, and result primarily from damage to the nerve fibres that carry messages up and down the spinal cord.

Despite the clinical diagnosis of "neurologically complete SCI", the spinal cord itself is rarely transected, as demonstrated by routine post-mortem histopathological investigations that have characterized the anatomical integrity of the lesion site. These observations have been corroborated by more recent noninvasive magnetic resonance imaging techniques, which have correlated changes in spinal cord tissue in the living patient with the gross clinical histopathology obtained post-mortem.

In this regard, there is increasing clinical and experimental evidence for significant preservation of descending tracts in neurologically complete SCI. In fact, use of the potassium channel blocker, 4-aminopyridine, in chronic spinal-injured cats and more recently in patients, provides strong evidence for the persistence of anatomically intact but physiologically dysfunctional descending supraspinal pathways. These drug studies in humans and in animals suggest that even though these remaining intact nerve fibres are dysfunctional, they may be induced to regain some physiologically significant function with the appropriate pharmacological intervention.

One of the histopathological hallmarks of traumatically injured spinal cord, in both clinical and experimental studies, is the presence of a central region of cavitation and necrosis (cell death), and a surviving subpial rim of tissue, composed predominantly of axons. Several theories have been proposed to account for these observations, including mechanical and vascular vulnerability of the central grey matter. However, remarkably little attention has been paid to why axons around the perimeter of the injured spinal cord survive, although morphometric analyses clearly indicate a direct relationship of axonal survival to pial depth.

Thus, it would be of considerable value to determine the factors that allow nerve fibres located around the periphery of the cord to survive while those located more centrally do not. Identification of the factors or mechanisms that allow nerve fibre survival, particularly during the early post-injury period, could possibly enable specific drug therapies to be targeted to maximize neurologic recovery in acute post-SCI cases.

There is substantial evidence in the literature that following the initial mechanical impact of traumatic CNS and spinal cord injuries, sequential and progressive tissue damage occurs at the injury site. These observations have given rise to the secondary injury hypothesis which implicates a cascade of neuropathological mechanisms in the post-traumatic destruction of spinal cord tissue. Included in the list of secondary injury mechanisms are post-traumatic ischemia and the release of excitotoxic amino acids.

Death of neurons following traumatic or ischemie disorders has been related to excess intracellular calcium which occurs, for example through excessive activation of post-synaptic glummate receptors (1,2). Considerably less is known about glial cell death, although electrophysiological and pharmacological studies indicate that glial cells probably do not have the same complement of glummate receptors as do neurons.

Glummate, a major excitatory neurotransmitter in the CNS, plays an important role in both neuronal plasticity and neurotoxicity (3). The diverse physiological functions of glutamate are reflected by the presence of distinct glutamate receptors (GluRs), which have been categorized into two major groups termed ionotropic and metabotropic (4). While ionotropic GluRs comprise integral cation-specific ion channels, the metabotropic family is coupled to intracellular signalling pathways via G-proteins.

Recent molecular (5,6) and immunocytochemical (7,8) studies have described the existence and CNS distribution of several different metabotropic glutamate receptor (mGluR) subtypes. Expression cloning (9,10), homology screening (5,11,12)) and the subsequent functional characterization of these cloned receptors have demonstrated at least seven different subtypes (13,15). The characterization of mGluR physiology and function has been hampered by the lack of specific agonists and antagonists, although the potential suitability of a number of recently synthesized phenyl glycine derivatives has been reported (16,17).

Extensive electrophysiological and pharmacological studies have implicated mGluRs in long-term changes in neuronal signalling such as learning and memory, as well as in several neuropathological states such as epilepsy and ischemia (13). Most of the reports in the literature have clearly indicated that over-activation of GluRs leads to neuronal death or dysfunction (13,17,18).

In contrast to the vast majority of reports in the literature, there have been two studies suggesting a neuroprotective effect of mGluR activation against putative NMDA-induced neuronal damage in vitro and in vivo (19,20). Publication (20) looked at choline acetyl transferase levels after intraocular injection of NMDA with or without a non-specific mGluR agonist (trans-ACPD [(1S-cis)-1-amino-1, 3-cyclopentanedicarboxylic acid]). A neuroprotective effect of trans-ACPD following focal cerebral ischemia in the mouse has also been reported (21). However, in none of the above studies, has the cell type, i.e., neuronal or glial, or the mGluR subtype been identified.

While major research efforts have been directed at an understanding of mGluR roles in neuronal cells, comparatively less information is available for glia, although there is pharmacological evidence to support the presence of mGluRs on astrocytes in culture (18).

There thus remains, at present, a serious deficiency in the in vivo treatment of traumatic injury to mammalian CNS tissue and, particularly, mammalian spinal cord injuries.

REFERENCE LIST

The present specification refers to the following publications, each of which is expressly incorporated by reference herein.

PUBLICATIONS:
1. Choi, D. W. and Rothman, S. M. (1990) The role of glutamate neurotoxicity in hypoxicischemic neuronal death. Ann. Rev. Neurol. 13:171–182.
2. Young, W. (1992) Role of calcium in central nervous system injuries. J.Neurotauma 9(suppl):s9–s25.
3. Meldrum, B. and Garthwaite, J. (1990) Excitatory amino acid neurotoxicity and neurodegenerative disease. TIPS 11:379–387.
4. Gasic, G. P. and Hollman, M. (1992) Molecular neurobiology of glutamate receptors. Annu. Rev. Physiol. 54:507–36.
5. Tanabe, Y., Masu, M., Ishii, T. et al. (1992) A family of metabotropic glummate receptors. Neuron 8:169–179.
6. Shigemoto, R. Nakanishi, S. and Mizuno, N. (1992) Distribution of the mRNA for a metabotropic glummate receptor (mGluR1) in the central nervous system: An in situ hybridization study in adult and developing rat. J. Comp. Neurol. 322:121–135.
7. Martin. L. J., Blackstone, C. D., Huganir, R. L. and Price, D. L. (1992) Cellular localization of a metabotropic glummate receptor in rat brain. Neuron 9:259–270.
8. Hampson, D. R., Theriault, E., Huang, X. et al. (1994) Differential distribution and developmental expression of two alternatively spliced forms of a metabotropic glummate receptor. Neuroscience.
9. Houamed, K. M., Kuijper, J. L., Gilbert, T. L. et al. (1991) Cloning, expression and gene structure of a G protein-coupled glummate receptor from rat brain. Science 252:1318–1321.
10. Masu, M. Tanabe, Y., Tsuchida, K. et al. (1991 ) Sequence and expression of a metabotropic glutamate receptor. Nature 349:760–765.
11. Abe, T., Sugihara, H. Nawa, H. et al. (1992) Molecular characterization of a novel metabotropic glutamate receptor mGluR5 coupled to inositol phosphate/Ca signal transduction. J. Biol. Chem. 267:13361–13368.
12. Pin, J-P, Ahem, S and Jolly, C (1993) Metabotropic glutamate receptors: Differences from other G-protein coupled receptors. J. Neurochem. 61 (Suppl.), S117D.
13. Nakanishi, S. (1992) Molecular diversity of glutamate receptors and implications for brain function. Science 258:597–603.
14. Birse, E. F., Eaton, S. A., Jane, D. E., et al. (1993) Phenylglycine derivatives as new pharmacological tools for investigating the role of metabotropic glutamate receptorsin the central nervous system. *Neurosci.* 52 (3):481–488.
15. Saugsmd, J. A., Kinzie, J. M., Mulvihill, E. R., et al. (1994) Cloning and expression of a new member of the L-2-amino-4-phosphonobutyric acid-sensitive class of metabotropic glutamate receptors. Mol. Pharmacol. 45:367–372.
16. Bashir, Z. L., Bartolotto, A. Z., Davies, C. H. et al. (1993) Induction of LTP in the hippocampus needs synaptic activation of glutamate metabotropic receptors. Nature 363:347–350.
17. Schoepp, D., Bockaert, J. and Sladeczek, F. (1990) Pharmacological and functional characteristics of metabotropic excitatory amino acid receptors. TIPS 11:508–515.
18. Conn, P. J. and Desai, M. A. (1991) Pharmacology and physiology of metabotropic glutamate receptors in the mammalian central nervous system. Drug Develop. Res. 24:207–229.
19. Koh, J. Y., Palmer, E. and Cotman, C. W. (1991) Activation of the metabotropic glutamate receptor attenuates n_methyl-D-aspartate neurotoxicity in cortical cultures. Proc. Natl. Acad. Sci. 88:941–9435.
20. Siliprandi, R., Lipartiti, M., Fadda, E. et al. (1992) Activation of the glutamate metabotropic receptor protects retina against N-methyl-Daspartate toxicity. European J. Pharmacol. 219:173–174.
21. Chiamulera, C., Albertini, P., Valerio, P. et al. (1992) Activation of metabotropic receptors has a neuroprotective effect in a rodent model of focal ischemia. Eur. J. Pharmacol. 216, 335–336.
22. Theriault, E. and Landis, D. M. D. (1987) Morphology of striatal neurons containing VIP-like immunoreactivity. J. Comp. Neurol. 256:1–13.
23. Hampson, D. R., Wheaton, K. D., Dechesne, C. J., et al. (1989) Identification and characterization of the ligand binding subunit of a kainic acid receptor using monoclonal antibodies and peptide mapping. J. Biol. Chem. 264:13329–13335.
24. Pickering, D. S., Thomsen, C., Suzdak, P. D., et al. (1993) Characterization of two alternatively spliced forms of a metabotropic receptor. J. Neurochem. 61:85–92.
25. Rivlin, A. S. and Tator, C. H. (1978) Effect of duration of acute spinal cord compression in a new acute cord injury model in the rat. Surg. Neurol. 10:39–43.
26. Theriault, E. and Tator, C. H. (1994) Persistence of rubrospinal projections following spinal cord injury in the rat. J. Comp. Neurol. 342:249–258.
27. Fehlings M. G., Tator C. H., Linden R. D., et al. (1987): Motor evoked potentials recorded from normal and spinal cord-injured rats. Neurosurgery 20: 125–130.
28. Fehlings M. G., Tator C. H., Linden R. D.: The relationships among the severity of spinal cord injury, motor and somatosensory evoked potentials and spinal cord blood flow. EEG Clinical Neurophysiol 74: 241–259, 1989.
29. Fehlings, M. G. and Nashmi, R. (1995). Assessment of axonal dysfunction in an in vitro model of acute compressive injury to adult rat spiral cord axons. Brain Res. (in press).
30. Fehlings M. G. and Tator C. H.: The effect of direct current field polarity on recovery after experimental spinal cord injury. Brain Research 579: 32–42, 1992.
31. Anthes, D. L., Fehlings, M. G., Theriault, E. and Tator, C. H. (1993) Development and validation of a model for multimodality assessment of electrophysiological function in the rat spinal cord. Eleventh Annual Neurotrauma Society Meeting, Nov. 6–7, 1993, Washington, D.C. (abstract)
32. Anthes, D. L., Fehlings, M. G., Theriault, E., Seth, R. and Tator, C. H. (1993) Electrophysiological and ultra-structural consequences of in vivo calcium ionophore exposure in the rat spinal cord. Soc. Neurosci. 19:1876 (Abstract #766.11).
33. Theriault, E., Hampson, D. R. and Tator, C. H. (1993). Distribution of a metabotropic glutamate receptor following acute traumatic spinal cord injury in the rat. 2nd International Neurotrauma Symposium, Jul. 4–9, 1993, Glasgow, Scotland.
34. Theriault, E. and Hampson, D. (1993) Differential distribution of two metabotropic glutamate receptor subtypes in the rat spinal cord. Soc. Neurosci. 19:748 (Abstract #308.1).
35. Theriault, E. (1993) Role of radial glia in axonal survival after spinal cord injury. 5th Int'l Symposium on Neural Regeneration, Dec. 8–12, 1993, Asilomar Conference Centre, Pacific Grove, Calif. (Abstract P59).
36. Baude, A., Nusser, Z., Roberts, J. D. B., et al., (1993) The metabotropic glutamate receptor (mGluR1α) is concentrated at perisynaptic membrane of neuronal subpopulations as detected by immunogold reaction. *Neuron* 11, 771–787.

37. Sacaan, A. and Schoepp, D. D. (1993). Activation of hippocampal metabotropic excitatory amino acid receptors leads to seizures and neuronal damage. Neurosci. Lett. 61:683–689.

SUMMARY OF THE INVENTION

It is an object of the present invention to provide in its broadest aspect a method of reducing the damaging effect of a traumatic injury to mammalian CNS tissue.

In a further object, the invention provides pharmaceutical compositions for use in treating mammals to reduce the damaging effect of a traumatic injury to mammalian CNS tissue.

The present invention is based on a discovery of a neuroprotective effect against acute, traumatic CNS and spinal cord injury by the manipulation of metabotropic glutamate receptor activation on subpial astrocytes. This discovery is applicable to all neuronal and glial cell types and further addresses the possibility that neurotoxicity results from the accumulation of toxic molecules and ions in the immediate neuronal environment.

Surprisingly, I have discovered that in contrast to the vast majority of the reports in the literature, activation of the mGluR, particularly the mGluR-1α subtype, is extremely neuroprotective following traumatic spinal cord injuries using in vivo and in vitro in preparations.

Accordingly, the invention provides in one aspect an in vivo method of reducing the deleterious effect of traumatic CNS tissue injury by applying to said tissue a therapeutically effective amount of a metabotropic glutamate receptor agonist.

Preferably, the agohist activates a mGluR sub-type, and more preferably the mGluR-1α subtype.

A preferred agohist is phenyl glycine and a most preferred agonist is trans-ACPD.

In a further aspect the invention provides a therapeutic composition for reducing the deleterious effect of in vivo traumatic CNS tissue injury comprising a therapeutically effective amount of a metabotropic glutamate receptor agonist and a pharmaceutically acceptable carrier, diluent or adjuvant therefor.

BRIEF DESCRIPTION OF THE DRAWINGS

In order that the invention may be better understood a preferred embodiment of the invention will now be described by way of example only with reference to the accompanying drawings wherein:

In more detail, FIGS. 1A and 1B show the in vivo effect of trans-ACPD on somatosensory evoked potentials. FIG. 1A is after a 35 g clip compression injury of the cord at C7-T1, the SSEP response was abolished and did not recover. After administration of trans-ACPD, there was significant recovery of the SSEP to indicate a neuroprotective effect. FIG. 1B shows the amplitude of the SSEP (mean of 14 experiments: means normalized to pre-injury) plotted as a function of time. Superfusion of the dorsal aspect of the cord with trans-ACPD promoted recovery of the SSEPs (conducted principally by superficial dorsal columns).

FIGS. 2A–2D in more detail provide the following information. FIG. 2A rats were decapitated and 30 mm segments of thoracic spinal cord dissected and placed in 5°–7° C. oxygenated Ringers. A 20 mm strip of dorsal column was then excised. Area X denotes dorsal column segment (including adjacent dorsal horn gray matter). In FIG. 2B, the isolated dorsal column was secured in a recording chamber as shown. Compound action potentials were recorded at 2 points with glass microelectrodes. The responses were displayed on an ocilloscope and digitized for computer-assisted analysis. Method of analysis of peak-peak amplitude and latency is as shown in FIG. 2C. The conduction time across the injury site was estimated from two point recording as shown in FIG. 2D.

With reference to FIGS. 3A–3D, field potential were recorded from isolated dorsal column segments from adult spinal cords (FIG. 3A, FIG. 3C). Injury was created in vitro by compression of the dorsal column segment with a 2 g clip for 15 seconds (FIG. 3B, FIG. 3D). The control preparation showed a characteristic attenuation of amplitude and prolongation of response latency with this injury (FIG. 3B). Pretreatment with the mGluR agonist trans-ACPD (100 nM) largely prevented the amplitude and latency changes after a similar injury, to indicate a neuroprotective effect (FIG. 3D).

FIG. 4A shows the relation of average group rank to overall average rank on the Tarlov Scale from the in vivo study of the effects of trans-ACPD. Rats received 35 g compression injuries, (C7-T1), followed by intravenous injections (0.5 mL) of either vehicle (ACSF) or trans-ACPD (at either 0.03 mg/Kg or 0.3 mg/Kg) 30 minutes post-injury. Animals were monitored weekly and Tarlov scores for each treatment group were subjected to Krushkal-Wallis analysis, which tests the equivalence of sample medians. A weekly z value for each group's rank on the Tarlov scale was derived and plotted against survival time. The resulting curve demonstrates trends in the correlation of locomotor recovery with drug administration. Animals receiving 0.03 mg/Kg trans-ACPD demonstrated higher Tarlov scores than those in the other groups.

FIG. 4B is a Rostro-Caudal profile of cavitation in cGR series cards. The volume of the spinal cord lesion site was 3-dimensionally reconstructed using camera lucida drawings and computer-assisted image analysis methodologies in animals shown above in (FIG. 4A). Animals with the better neurological scores i.e. the group receiving 0.03 mg/Kg trans-ACPD had a larger volume of cavitation at the site of the lesion, and thus possibly less necrotic and dysfunctional tissue left at the epicentre and slightly caudal to it. All evaluations and data analysis in these experiments were performed without knowledge of the treatment groups.

DETAILED DESCRIPTION OF THE INVENTION

EXPERIMENTAL

Figure 1A:
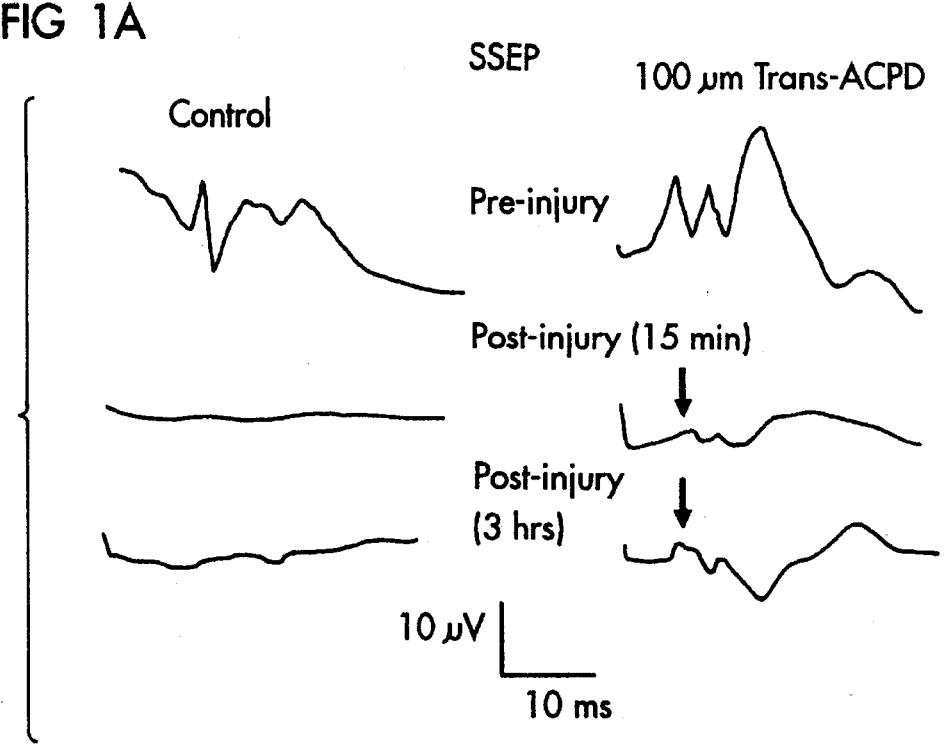
FIGS. 1A and 1B show recordings of somatosensory evoked potentials (SSEPs) in vivo.

MATERIALS AND METHODS
(A) ANATOMICAL STUDIES

Immunocytochemistry (Series 1): Adult female Wistar rats (n=6) were overdosed with a barbiturate anaesthetic, sodium pentobarbitol, and perfused transcardially with a fixative, 4% paraformaldehyde, in phosphate buffer. A laminectomy was performed, the cervical enlargement of the spinal cord was removed, and 30 μm thick sections of the cord were cut on a vibratome. Rabbit polyclonal antisera was obtained following immunization of the animals with peptides corresponding to unique amino acid sequences in the carboxy terminus of two different mGluR1 subtypes. The antisera were gifts from Eileen Mulvihill, Zymogenetics, Seattle, Wash. (cf,9). Tissue sections were reacted free-floating as previously described (8,22), and diamino benzidine was used as the chromogen to visualize the reaction product. Control experiments included omission of the primary antisera or adsorption with the subtype-specific peptide sequence. Importantly, both procedures resulted in an absence of immunoreactivity. It is noted that these findings have since been replicated using other well-characterized antisera to mGluR-1α from other labs (gifts from Richard Huganir in Baltimore, Md. and from Ryuichi Shigemoto in Kyoto, Japan).

Electrophoresis and Immunoblotting: Sodium dodecyl-sulfate polyacrylamide gels (SDS-PAGE) and immunoblotting procedures were carried out as previously described (23). A goat anti-rabbit IgG conjugated to alkaline phosphatase (Promega) was used as the secondary antibody. Spinal cord tissue samples were prepared for SDS-PAGE by homogenizing freshly dissected, snap frozen regions of the cord in SDS sample buffer and heated prior to application to the gel (9). Crude membrane fractions prepared from baby hamster kidney cells (BHK 570) expressing the mGluR1α subtype were prepared in the same manner. The production and characterization of these cell lines have been described (24).

Immunocytochemistry (Series 2): The clip compression model of spinal cord injury (SCI) in adult Wistar rats was used (25,26), resulting in anatomical and functional losses equivalent to those found in traumatic human SCI: The anaesthetic and surgical techniques have been described in detail (26). Briefly, under halothane anaesthesia a cervical (C7-T1) laminectomy was performed and the spinal cord at C8/T1 was extradurally compressed for one minute between the blades of a modified aneurysm clip, calibrated to deliver a closing force of 50 gm. This is a well-documented, reproducible model of severe SCI which results in paraplegia or severe paraparesis (25,26,27,28). Animals (n=6) were sacrificed 24 hours later and the spinal cord tissue prepared for immunocytochemistry as described above.

In vivo Electrophysiology Experiments (Series 3): In vivo rat spinal cord preparations were developed and characterized for recording MEPs and SSEPs from the anaesthetized adult female Wistar rat in order to assess the neurophysiological integrity of the spinal cord (27,28). It has been demonstrated that these responses reflect the severity of injury accurately, predict recovery of clinical neurological function, detect functional improvement sensitively, and are correlated with changes in spinal cord blood flow (27,28). Importantly, these evoked responses can be recorded from rats with chronic SCI, by using permanently implanted extradural screw electrodes, thus permitting serial electrophysiological studies (30).

Figure 1B:
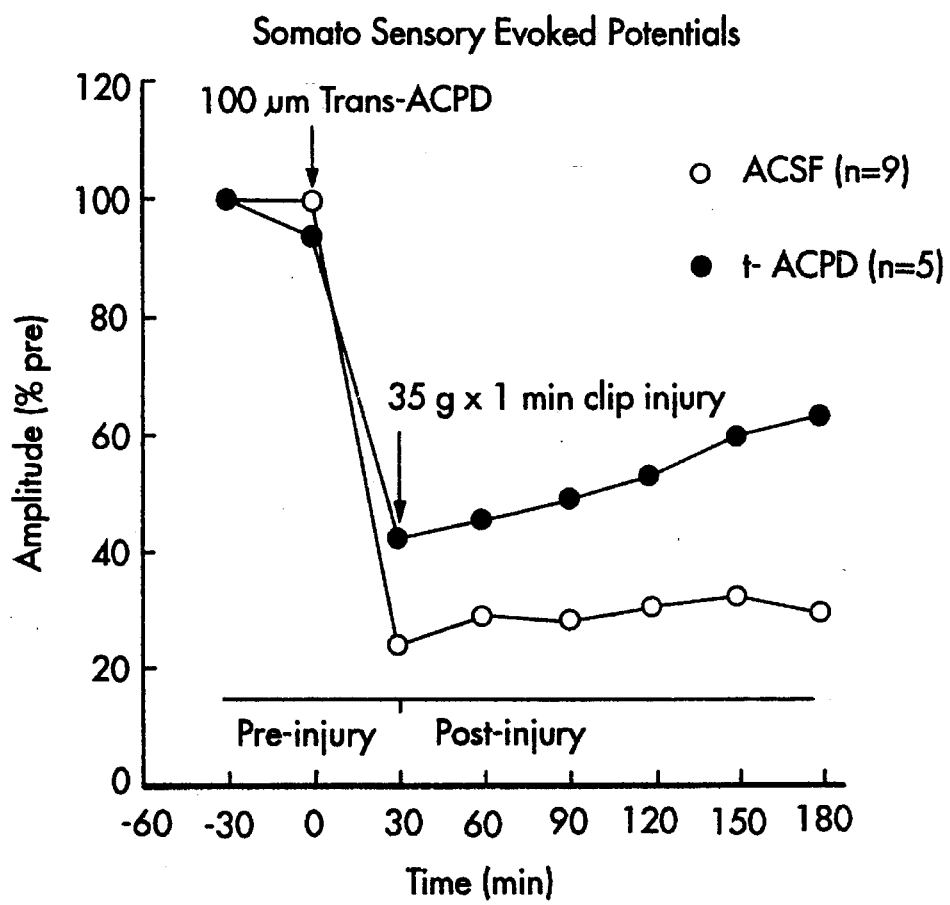
Figure 2A:
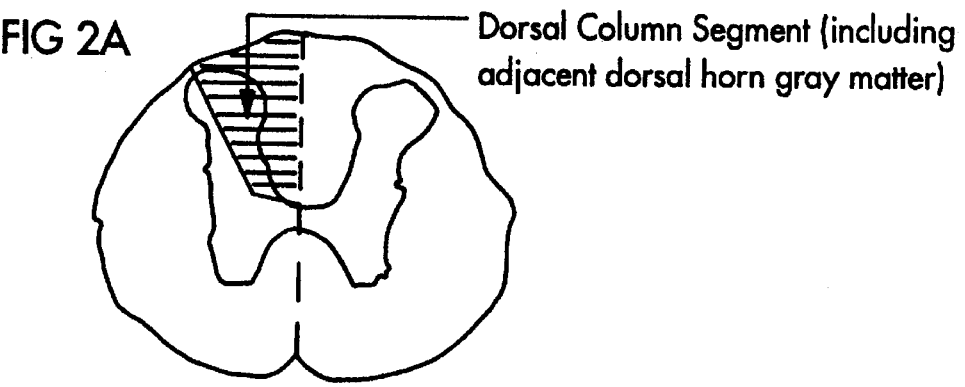
FIG. 2A represents a diagrammatic perspective view of a transverse section of a rat spinal cord.
Figure 2B:
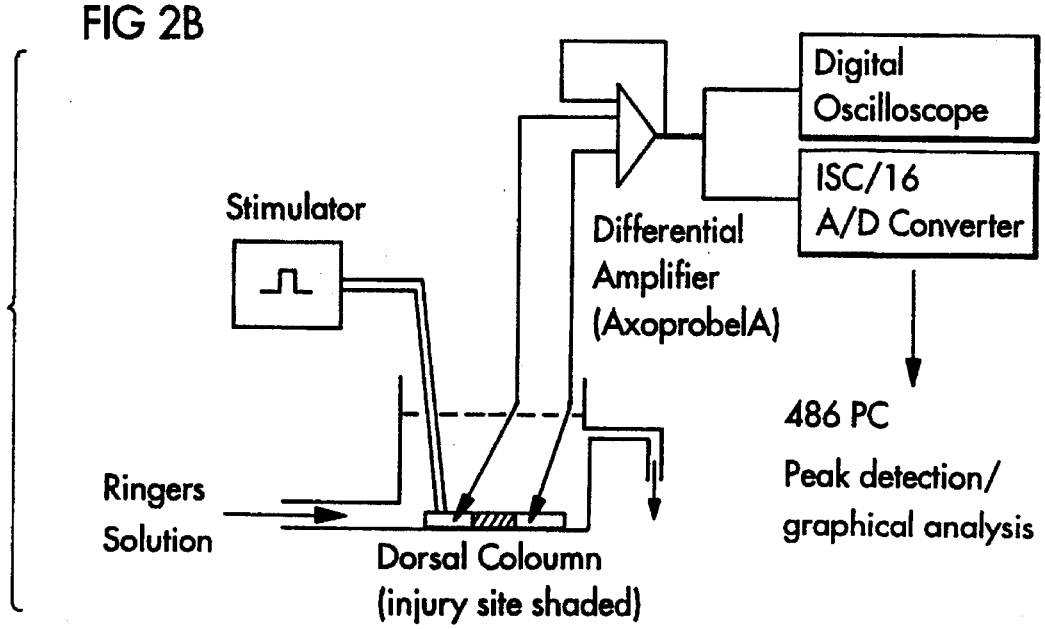
FIG. 2B represents a block diagram of apparatus used to record in vitro electrophysiologic parameters of spinal cord axons.
Figure 2C:
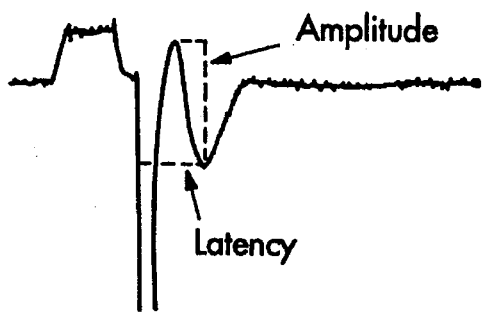
FIG. 2C shows a graph of the amplitude and latency of a field potential against time in a collection of axons from a single electrode on uninjured tissue.
Figure 2D:
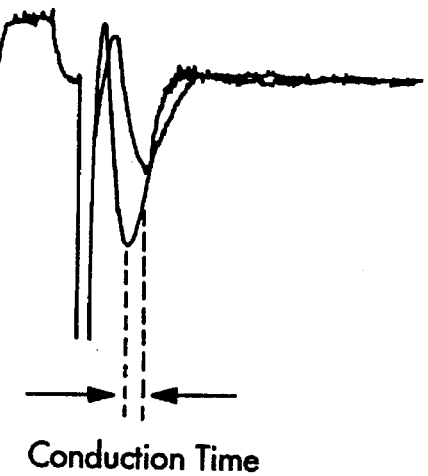
FIG. 2D shows a graph of the amplitude of field potentials against time in a collection of axons from two electrodes placed across injured tissue.
Figure 3A:
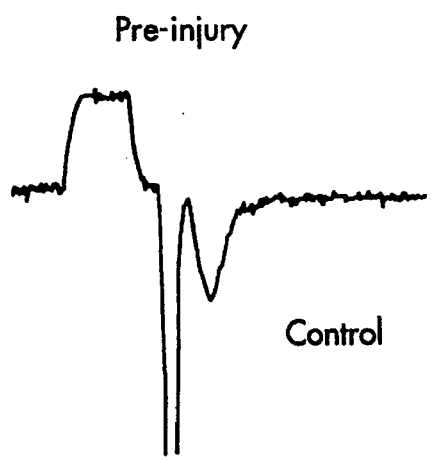
FIG. 3A shows in vitro recordings of field potentials from isolated rat dorsal column segments.
Figure 3B:
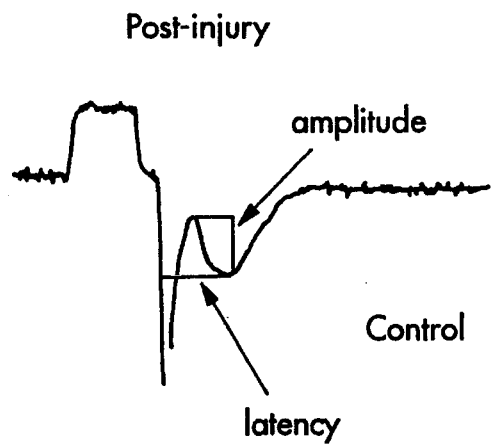
FIG. 3B shows similar recordings following in vitro injury.
Figure 3C:
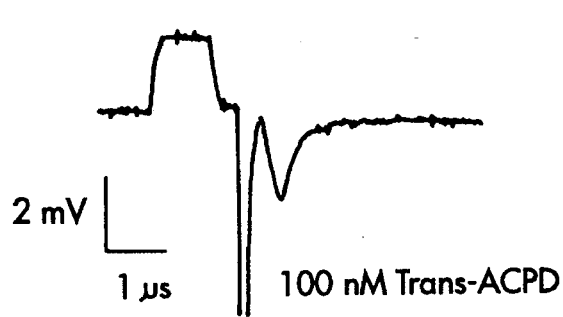
FIGS. 3C and 3D show in vitro recordings of field potentials in isolated rat spinal cord segments taken pre- (3C) and post-injury (3D) in the presence of a mGluR agonist.
Figure 3D:
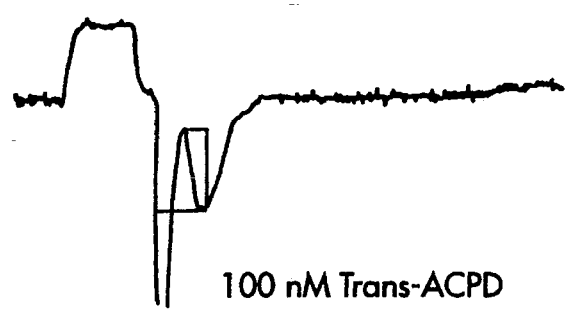

In the studies of the present invention, somatosensory evoked potentials (SSEPs) were recorded from injured animals (n=5) and normal animals (n=9) by techniques previously described (28,30). In brief, SSEPs are recorded from the spinal cord and sensorimotor cortex after direct bipolar stimulation of the exposed sciatic nerve (10 mA, 100 μs, 4 Hz). Responses are recorded at a band width of 30–3000 Hz and averaged (Clarke-Davis signal averager). A 100 μM concentration of trans-ACPD was prepared in artificial cerebrospinal fluid (ACSF) and applied according to a protocol developed in our lab (31). Briefly this consisted of superfusing the pial surface of the spinal cord with 400 μL of the drug at 37° C., 30 minutes prior to a 35 gm clip compression injury. Results are shown in FIG. 1.

In vitro Electrophysiology Experiments (Series 4): With reference to FIGS. 2A–2D, the technique for in vitro electrophysiological recordings from longtitudinal slices of adult rat spinal cord has been previously described (29). Briefly, a 20 mm length of dorsal column from the thoracic cord was isolated and placed in a temperature-regulated recording chamber. In addition to recording field potentials with analysis of amplitude, latency and conduction velocity, refractory periods were estimated by double pulse techniques, and the effect of train stimulation examined. Preliminary studies of membrane potential changes in axons after traumatic injury have been conducted using the sucrose gap technique and indicate that acutely injured axons display a number of important physiological abnormalities, including reduced conduction velocity, an increase in the relative and absolute refractory periods, ouabain-resistant high frequency conduction failure and conduction block at subphysiological temperatures. In addition, a highly reproducible method of injuring the dorsal column segment in vitro using a modified aneurysm clip with a closing force of 2 gm has been developed (FIG. 2).

The technique for isolating a segment of dorsal column from the rat cord, the composition of the Ringer's solution, and the stimulation and recording conditions have been described (29). Field potentials were recorded at two points with glass microelectrodes (1M NaCl; 1–2 MΩ). The latency, amplitude, conduction time and conduction velocity were assessed as described, and frequency-dependent changes in axonal conduction were assessed by conventional and random double pulse train stimulation (29). In these studies, a 100 nM solution of trans-ACPD was bubbled with 95–5 % $CO_2/O_2$ and superfused over the surface of spinal cord slices (n=4). Electrophysiological measurements were made before and after application of the clip injury.

Figure 4A:
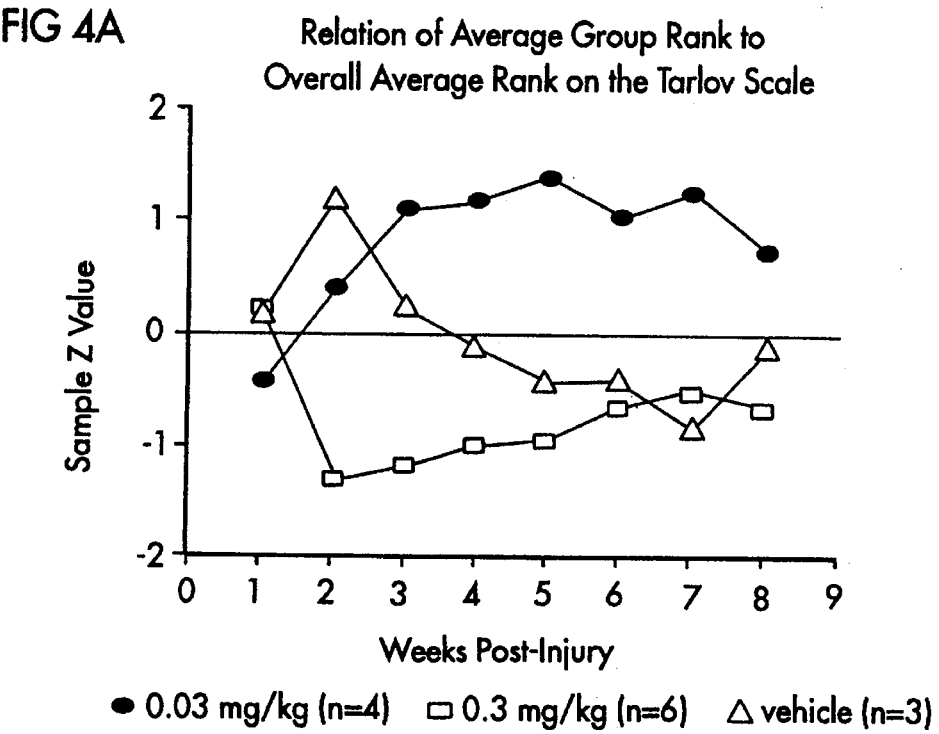
FIG. 4A shows a correlation of locomotor recovery with drug administration in animals given 0.03 mg/kg of trans-ACPD 30 minutes after SCI by an intravenous injection.
Figure 4B:
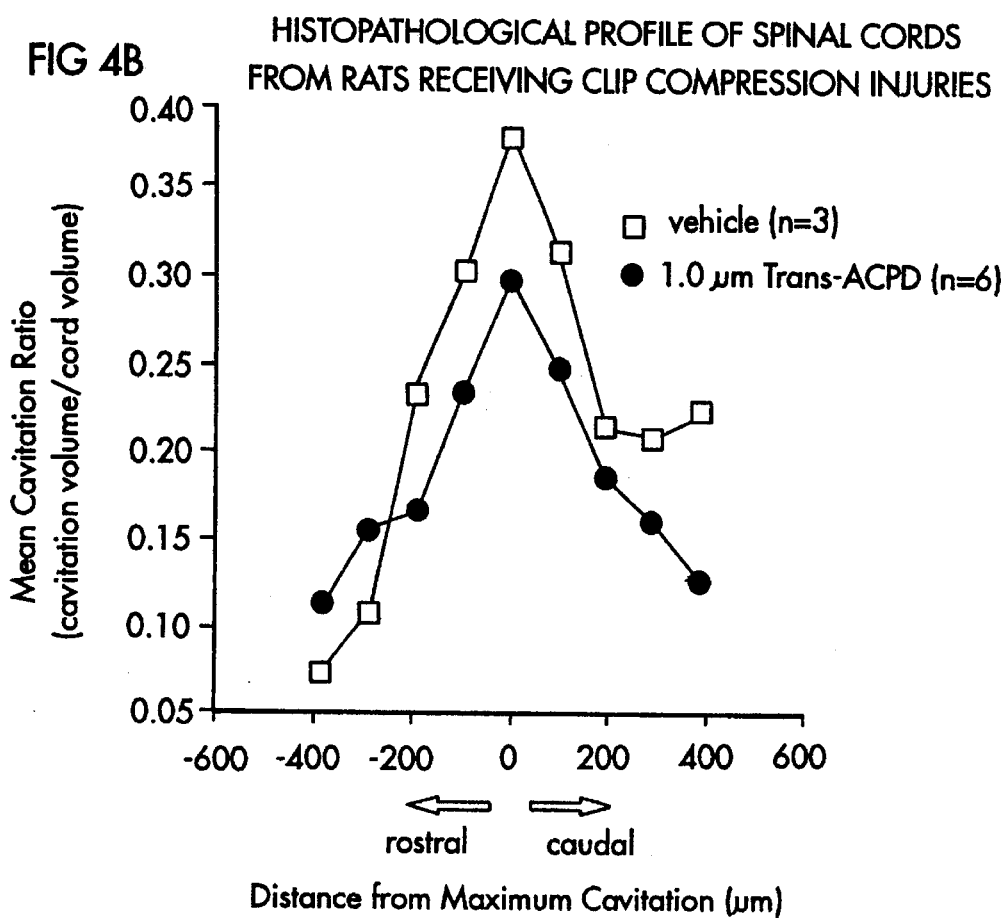
FIG. 4B shows the relationship of the spinal cord histology and the drug treatment groups.

In vivo Chronic Survival Experiments (Series 5): SCI was performed as described above in 13 animals. Thirty minutes after injury, each animal received a single 0.5 ml tail-vein injection of either vehicle ACSF, n=3 or trans-ACPD at either 0.03 mg/Kg, n=4; or 0.3 mg/Kg, n=6. Neurological performance was assessed weekly using the inclined plane technique and the modified Tarlov scale (25, 26, 30) until sacrifice at 8 weeks post-SCI. The spinal cord tissues were harvested, serially sectioned and the site of the injury was 3-dimensionally reconstructed using camera lucida drawings and computer-assisted image analysis techniques (26). All evaluations and data analysis were done in a blinded fashion, so at every stage the experimenters were unaware of the treatment groups of the animals. The results are shown in FIGS. 4A and 4B.

RESULTS

Immunocytochemistry (normal spinal cord): The immunocytochemical findings were totally opposite to that expected, in that only a small population of non-neuronal cells or glia, around the periphery of the spinal cord was stained by the anti-mGLuR-1α antisera (33,34).

Strong immunoreactivity at the pial surface of the spinal cord, was observed where the radial processes of a population of glia (astrocytes), terminate. Surprisingly, there was no staining of cell bodies, of either neuronal or glial morphology, in the grey matter.

In studies where sections were reacted for both mGluR1α and glial fibrillary acidic protein (GFAP; a specific marker for astrocytes; anti-GFAP antisera obtained from Dakopatts, Dimension Laboratories, Mississauga, Ontario) GFAP-positive astrocytes with a radial morphology were found to be immunoreactive for the mGluR1α subtype.

Electrophoresis and Immunoblotting: In order to verify the presence of specific immunoreactivity seen in cross-sections of the fixed rat spinal cord, Western blots were done on spinal cord tissue and run alongside tissue prepared from cells transfected with the mGluR1α DNA (34). The results revealed immunolabelling of a protein with a relative molecular weight of 154 kilodaltons (kDa), corresponding to the identified weight of the mGluR-1α receptor. The lack of cross-reactivity of the antibodies with other mGlu receptor subtypes (including mGluR1β) has been described in previous reports (8) so that immuno-labelling of this protein in the spinal cord represented the presence of specific mGluR1α epitopes recognized by the antisera (34).

Immunocytochemistry (injured spinal cord): The zone of tissue around the SCI lesion site (the "ischemic penumbra") contains cells "at risk", in other words, cells that have sustained damage to varying extents and which may or may not go on to survive. In studies of this ischemic penumbra region it was found that the staining intensity for mGluR1α was greatly increased, particularly in the subpial zone, i.e., in the region of the spinal cord which usually survives (33,34).

DISCUSSION

In contrast to previous studies which identified mGluR1α immunoreactivity on neuronal profiles in CNS regions including the hippocampus and cerebellum (8,36), the present results show that the pattern of mGluR1α staining in the spinal cord is distinctly different, in that primarily astrocytic cell bodies and their processes are immunoreactive (33,36). The differential distribution of metabotropic glutamate receptor subtypes on glia, and indeed, on different glial subpopulations, either in the brain or spinal cord has not been well documented nor is the possible functional significance of these receptors fully understood.

In the rat CNS, there is evidence for the co-localization of mGluR1α immunoreactivity with a population of somatostatinergic neurons in the hippocampus (8,36). These results indicate that distinctive patterns of mGluR distribution are likely to be manifest in different regions of the CNS.

Electrophysiological results investigating the effect of application of a mGluR agohist trans-ACPD to the injured rat spinal cord in vivo (in the intact animal) demonstrated a neuroprotective effect of the drug on the recovery of evoked potentials (to approximately 40% of normal) up to three hours after spinal cord injury (FIG. 1). The results obtained from untreated animals showed the SSEP response was abolished after SCI and did not recover.

Superfusion of trans-ACPD in vitro (in the spinal cord slice preparation) provided a neuroprotective effect consistent with the results obtained in vivo (FIG. 3). Control preparations showed a characteristic attenuation of amplitude and prolongation of response latency with injury. Treatment of the spinal cord preparation with the mGluR agonist trans-ACPD (100 nM) largely prevented these field potential changes, preserving the amplitude up to 76% of normal.

In contrast to the vast majority of reports in the literature, there have been two studies suggesting a neuroprotective effect of mGluR activation against putative NMDA-induced neuronal damage in vitro and in vivo (19,20). The latter publication looked at choline acetyl transferase levels after intraocular injection of NMDA with or without a non-specific mGluR agonist (trans-ACPD[(1S-cis)-1-amino-1,3-cyclopentanedicarboxylic acid]). Another group has reported a neuroprotective effect of trans-ACPD following focal cerebral ischemia in the mouse (21). In none of these studies had the cell type (i.e., neuronal or glial) or the mGluR type been identified, however. In fact the use of mGluR agonists for treatment of any type of CNS injury would seem to be counter-intuitive based on the vast majority of the prior literature.

While the invention has been described in detail and with reference to specific embodiments thereof, it will be apparent to one skilled in the art that various changes and modifications can be made therein without departing from the spirit and scope of the invention.

I claim:

1. An in vivo method of reducing the deleterious effect of traumatic CNS tissue injury by applying to said tissue a therapeutically effective amount of a metabotropic glutamate receptor agonist.

2. A method as claimed in claim 1 wherein said metabotropic glutamate receptor is selected from a mGluR sub-type.

3. A method as claimed in claim 2 wherein said mGluR sub-type is mGluR-1α.

4. A method as claimed in claim 1 wherein said agonist is phenyl glycine.

5. A method as claimed in claim 1 wherein said agonist is trans-1-amino-1,3-cyclopentane dicarboxylic acid.

6. A method as claimed in claim 1 wherein said CNS tissue injury is a spinal cord injury.

* * * * *